United States Patent
Bennouri et al.

(10) Patent No.: US 9,753,182 B1
(45) Date of Patent: Sep. 5, 2017

(54) MAPPING UV INDEX DATA MEASURED BY UV DOSIMETRY SYSTEM

(71) Applicants: Nabyl Bennouri, Tualatin, OR (US); Jie Lian, Beaverton, OR (US); Nattapon Chaimanonart, Lake Oswego, OR (US)

(72) Inventors: Nabyl Bennouri, Tualatin, OR (US); Jie Lian, Beaverton, OR (US); Nattapon Chaimanonart, Lake Oswego, OR (US)

(73) Assignee: Ultra, Inc., Beaverton, OR (US)

( * ) Notice: Subject to any disclaimer, the term of this patent is extended or adjusted under 35 U.S.C. 154(b) by 621 days.

(21) Appl. No.: 14/257,778

(22) Filed: Apr. 21, 2014

Related U.S. Application Data (60) Provisional application No. 61/815,683, filed on Apr. 24, 2013.

(51) Int. Cl.
   *G01W 1/00* (2006.01)
   *G01N 31/00* (2006.01)
   (Continued)

(52) U.S. Cl.
   CPC .............. *G01W 1/02* (2013.01); *G01J 1/42* (2013.01); *A61B 5/441* (2013.01); *G01J 1/0219* (2013.01);
   (Continued)

(58) Field of Classification Search
   None
   See application file for complete search history.

(56) References Cited

U.S. PATENT DOCUMENTS

| | | | | |
|---|---|---|---|---|
| 5,401,970 A | * | 3/1995 | Kinsey | G01J 1/429 250/372 |
| 5,995,862 A | * | 11/1999 | Gallorini | A61B 5/0059 250/372 |

(Continued)

FOREIGN PATENT DOCUMENTS

WO   WO 2005036110 A1 * 4/2005 ............. G01D 21/00

OTHER PUBLICATIONS

Electric Power Group v. Alstom (Case Attached).*
(Continued)

*Primary Examiner* — Mohamed Charioui
*Assistant Examiner* — Leonard S Liang (57) ABSTRACT

A UV dosimetry system comprises a wearable unit and a mobile computing device. The wearable unit measures the UV irradiance intensity and wirelessly communicates with the mobile computing device. The UV dosimetry system supports multi-user control and can link one mobile computing device with multiple wearable units. The UV dosimetry system processes the measured UV irradiance intensity to calculate the UV index (UVI) and the sensor site specific UV dose. It can also calculate the total absorbed UV dose and vitamin D production by taking into account user specific factors. The UVI data measured by a plurality of UV meters such as the disclosed UV dosimetry system are crowd sourced to a remote server together with the location and time data of the measurement. The remote server excludes invalid UVI measurement and generates UVI maps showing time-varying distribution of UVI data at different locations.

20 Claims, 2 Drawing Sheets

(51) Int. Cl.
*G01B 5/28* (2006.01)
*G01B 5/30* (2006.01)
*G01W 1/02* (2006.01)
*G01J 1/42* (2006.01)
*A61B 5/00* (2006.01)
*G01J 1/02* (2006.01)
*G01J 1/44* (2006.01)

(52) U.S. Cl.
CPC .............. *G01J 1/0233* (2013.01); *G01J 1/429* (2013.01); *G01J 1/44* (2013.01)

(56) References Cited

U.S. PATENT DOCUMENTS

| | | | |
|---|---|---|---|
| 8,552,391 B2 | 10/2013 | Terenetska et al. | |
| 8,793,212 B2* | 7/2014 | McGuire | G06N 5/00 706/62 |
| 2004/0108191 A1* | 6/2004 | Su | G01J 1/429 200/61.02 |
| 2004/0149921 A1 | 8/2004 | Smyk | |
| 2004/0200967 A1* | 10/2004 | Russell | G01T 1/026 250/370.01 |
| 2004/0235431 A1* | 11/2004 | Jung | G08B 21/02 455/90.1 |
| 2006/0226371 A1* | 10/2006 | Lu | G01J 1/02 250/372 |
| 2006/0289779 A1* | 12/2006 | Marmaropoulos | G01D 21/00 250/372 |
| 2008/0231471 A1* | 9/2008 | Thorsted | G01J 1/429 340/952 |
| 2010/0096559 A1 | 4/2010 | Yao et al. | |
| 2011/0191052 A1* | 8/2011 | Lin | G01C 25/00 702/94 |
| 2011/0191272 A1 | 8/2011 | McGuire | |
| 2011/0276269 A1* | 11/2011 | Hummel | H02J 3/383 702/3 |
| 2012/0215446 A1* | 8/2012 | Schunder | G07C 5/008 702/3 |
| 2012/0326046 A1 | 12/2012 | Aslam | |
| 2013/0273921 A1* | 10/2013 | Kenington | H04W 16/18 455/446 |
| 2014/0093148 A1 | 4/2014 | Williams | |
| 2014/0195198 A1* | 7/2014 | Reshef | G06F 17/00 702/188 |
| 2015/0041663 A1 | 2/2015 | Oliver et al. | |
| 2015/0294080 A1* | 10/2015 | Garnavi | G06F 19/3431 702/19 |

OTHER PUBLICATIONS

Godar DE, Pope SJ, Grant WB, Holick MF. Solar UV doses of young Americans and vitamin D3 production. Environ Health Perspect Jan. 2012;120:139-143.

Pope SJ, Godar DE. Solar UV geometric conversion factors: horizontal plane to cylinder model. Photochem Photobiol Mar.-Apr. 2010;86:457-466.

Thieden E, Agren MS, Wulf HC. The wrist is a reliable body site for personal dosimetry of ultraviolet radiation. Photodermatol Photoimmunol Photomed. Apr. 2000;16(2):57-61.

* cited by examiner

MAPPING UV INDEX DATA MEASURED BY UV DOSIMETRY SYSTEM

CLAIM OF PRIORITY

This application claims the benefit of priority under 35 U.S.C.§119(e) of U.S. Provisional Application No. 61/815,683, entitled "UV DOSIMETRY SYSTEM", filed on Apr. 24, 2013, which is hereby incorporated by reference.

1. FIELD OF THE INVENTION

The present invention relates generally to a system and method for measuring the ultraviolet (UV) irradiation and usage of such information for calculating the UV index, UV dose and vitamin D production, and for mapping the measured UV index data.

2. BACKGROUND

Ultraviolet (UV) radiation is part of the electromagnetic spectrum that reaches the earth from the sun and has wavelengths shorter than visible light. These wavelengths are classified as UVA (320-400 nm), UVB (280-320 nm), or UVC (100-280 nm). While most UVC is absorbed by the ozone layer and does not reach the earth, both UVA and UVB can penetrate the atmosphere and have important health consequences.

Overexposure to UV radiation is the major risk factor for the development of skin cancer, which is the most common form of cancer in the United States. In addition, increased exposure to sun irradiation has been linked to immune suppression and eye damage. On the other hand, UV radiation in sunlight can also affect people's health in beneficial ways. In particular, sunlight is the major source of vitamin D producing UVB radiation, which has a wide range of positive health effects. Vitamin D production is not only important to prevent osteoporosis and osteomalcia, but also may decrease the incidence of diabetes, reduce the mortality from various cancers, among many other health benefits. However, a number of studies have shown that most American children, adolescents, and adults may not go outside enough to meet their vitamin D needs. Therefore, there has been a growing consensus among a number of public health organizations that there needs to be a balance between the risks of having too much and the risks of having too little sunlight.

UV index (UVI) is an internationally accepted parameter for measuring the intensity of UV radiation. However, measuring UVI alone is insufficient to determine if a person receives too little or too much UV exposure. The actual UV irradiation dose received by a person is not only affected by the UVI, but also affected by many other factors, such as the duration of UV exposure, the applied sunscreen, etc.

Most existing UV measurement instruments are ground based. While these instruments can provide broadband measurement of UV irradiance received by the UV sensor at the ground level, such a measurement is unlikely to reflect the actual UV irradiance received by individuals in the same area. Environmental factors such as cloud cover, tree or building shade, reflections from water, sand, snow, building, etc, as well as personal choices such as sunscreen usage can have substantial impact on the actual dose absorbed by the individual. Efforts have been made in recent years to develop wearable UV measurement devices. However, these UV measurement devices have a number of shortcomings, including but are not limited to: the device is cumbersome and not convenient for daily wearing; the device is not waterproof; the device can only measures the UVI, not the actual UV dose; the UV measurement does not take into account factors affecting skin UV absorption such as clothing coverage, skin color, sunscreen usage, sensor location, etc.; the device lacks capabilities for data storage, editing, analysis, and reporting; and the device lacks networking capability.

UV radiation in sunlight can also affect people's health in beneficial ways, in particular, vitamin D production. Many people do not get sufficient vitamin D from dietary sources, so sunlight-derived vitamin D is their primary source. However, because of the fear of developing skin cancer, many people avoid sunlight whenever possible and wear protective clothing and sunscreens. As a result, many people have vitamin D insufficiency. So far, there is no objective measure on the actual UV dose received by a person and how much vitamin D has been produced by the UV radiation. Thus people are unaware of whether they received too much or too little sunlight, and not sure how much vitamin D supplement should be taken—if it is needed at all.

Currently there is no information about the level of UVI at different places in real time, which could help people prepare or avoid exposing to a high UVI area. Although some weather stations might have a forecasted UVI data, the forecast is based on modeled simulation for a large geometrical area, and lacks both spatial resolution and temporal resolution. Moreover, there are several factors that make that data inaccurate. For example, the forecasted UVI does not include the effects of atmospheric pollutants or haze which can substantially decrease UV intensity, especially in urban areas. The forecast does not take into account variable surface reflection (e.g., sand, water, or snow), which can substantially increase individual's exposure at the beach or on ski-slopes.

Although there are some efforts to develop wearable UV measurement devices, these devices have a number of shortcomings. For example, the existing UV devices do not have the indications of device circuitry such as battery status, local memory status and electronic leash status, which could result in a delay of application program functions especially when some immediate actions such as user notification is needed. The sampled UV data could be lost, if the battery is running low or the local memory is full. In addition, multiple users could not share the same hardware since the user information is stored in the specific hardware. Many wearable UV measurement devices are for designed for single-user purpose. Parents wanting to monitor several children at the same time or a person who wants to measure UV at several different locations have to use multiple devices. Moreover, there is no intuitive summary for the users to understand their UV dose, and there is a lack of user editing or programming function. Furthermore, the operation of these devices is not convenient and user friendly.

The shortcomings of the existing UV measurement devices are solved by the present invention as described below. The unique advantages of the present invention will be appreciated by people of ordinary skill in the art after referring to the written description of the invention in conjunction with the illustrative drawings.

4. DETAILED DESCRIPTION

General Description of the System Components

According to this disclosure, the personal UV dosimetry system comprises a wearable unit and a mobile computing device. The wearable unit is a stand-alone, miniature device with aesthetic design, and is preferably waterproof. The wearable unit comprises a circuitry for measuring the irradiating UV intensity. Moreover, the wearable unit has a plurality of connecting mechanisms (e.g. clip, button, adhesive surface, etc.) that enable it to be easily adapted to be worn by an individual at various body parts. For example, the wearable unit can be worn as a clothing button, or a necklace, or wrist band, or hat accessory, etc. The wearable unit is capable of wirelessly and bi-directionally communicating with the mobile computing device, such as a smart phone or a tablet computer. As known in the art, the mobile computing device usually has rechargeable battery, a built-in camera, a location/navigation system such as the Global Positioning System (GPS), a user interface for receiving user input and generating various types of output, including but are not limited to, high resolution display, user notifications (e.g. via sound, vibration, text message, etc). The mobile computing device runs an operating system (e.g. iOS, Android, etc.) and is capable of wireless connection to a communication network. The mobile computing device has the software application that can display, store, edit, analyze, and provide summary report of the data collected by the wearable unit. The UV measurement data collected by the wearable unit and analyzed by the mobile computing device includes not only UVI, but also UV dose actually received by the subject and vitamin D production within a time period, taking into account of various factors such as skin type, sunscreen usage, sensor location, etc. In addition, the mobile computing device can simultaneously tracks multiple users and/or multiple wearable units.

Figure 1:
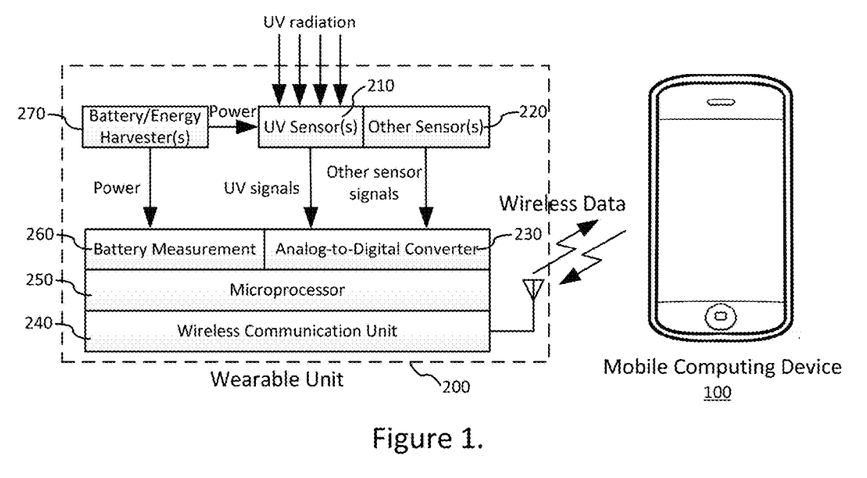
FIG. 1 shows the high level block diagram of the UV dosimeter system comprising a wearable unit and a mobile computing device.

FIG. 1 shows the high level block diagram of the UV dosimeter system comprising a wearable unit 200 and a mobile computing device 100. The UV radiation can be detected by built-in UV sensors 210, which transform incident radiant UV signals into standard electrical signals. Semiconductor UV sensors fabricated using Silicon, Silicon-Carbide, Gallium-Nitride, Gallium-Arsenide and Germanium may be used as UV sensors due to their wide band-gap properties. The UV signals corresponding to the UV radiation intensity may be further digitized by an analog-to-digital converter 230. Other sensors 220 such as temperature sensors and humidity sensors can be included into the unit for enhanced system features. All detected sensing signals are processed by a microprocessor 250, and the acquired sensor data can be temporarily stored in a local memory circuit. The arranged data is then wirelessly sent to the mobile computing device for post data processing. A wireless communication unit 240 employing a wireless technology standard such as Bluetooth technology can be used to wirelessly transmit and receive data between the wearable unit 200 and the mobile computing device 100. Battery cells 270 such as a battery button cell can be used to power the wearable unit 200. Energy harvesters such as thermal electric generator or solar cell can be used as an alternative source of energy to power the wearable unit. The battery measurement block 260 may be included for enhanced features including monitoring the battery usage and determining device false operating conditions.

General Description of the System Operation

Figure 2:
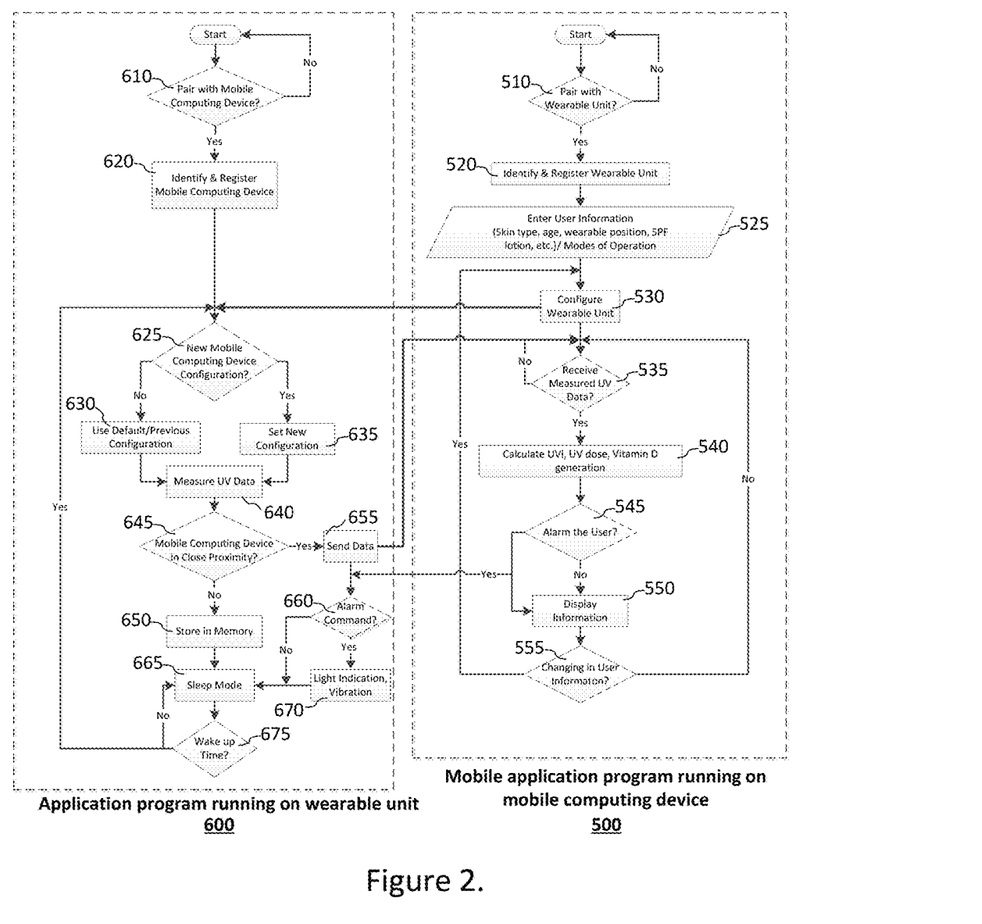
FIG. 2 shows the high level operation flowchart of the application software program running on the wearable unit and the application software program running on the mobile computing device, and the communication between thereof.

As shown in FIG. 2, the application program 600 running on the wearable unit controls the operation of the wearable unit 200. After the wearable unit 200 is turned on, the application program 600 starts advertising the data 610 through the wireless communication protocol 610 to pair with the mobile computing unit 100. The mobile application program 500 running on the mobile computing device 100 then tries to discover the advertising data pocket 510 to pair with the wearable unit 200. Once the broadcasting data is detected, an authentication process begins where both wearable unit 200 and mobile computing device 100 exchange the data to establish a connection. Several connection processes may be attempted until the connection is established, and the pair of wearable unit 200 and the mobile computing unit 100 identify and register with each other (620, 520) by respective application programs. The mobile application program 500 can notify users for a status of this pairing process. The mobile application program 500 can keep a record of the previous registered wearable units 200, thus the pairing process can be expedited in the future. Through the mobile application program 500, the user can edit modes of operation as well as personal information 525 such as the skin type, age, wearable position, and sun protection factor (SPF), etc. Some user information can be detected by employing a mobile computing peripheral unit. For example, the skin type may be detected by analyzing an image captured by a mobile computing camera. SPF lotion data can be detected by scanning the barcode on a lotion bottle. Based on received UV data 535 measured and sent from the wearable unit 200 and the entered user information 525, the mobile application program 500 can calculate the UVI, UV dose, and the amount of vitamin D production 540. Users can change the personal information 555 such as sunscreen usage and clothing coverage at any time so that the updated user information can be used for calculating UV dose and vitamin D production. User can also check the UV dose and related information such as vitamin D production through the mobile application program 500 anytime. The application program features will be described later in this disclosure. The wireless data communication between the wearable unit 200 and the mobile computing device 100 is automatically running in the background to make the mobile application program 500 user friendly and easy to use.

General Description of the Communication Protocol

Both mobile computing device 100 and wearable unit 200 are linked together through a communication protocol as demonstrated in the high level flowchart shown in FIG. 2. After the pairing connection process is established, the user programmable modes of operation 525 corresponding to commands and configurations for the wearable unit 200 such as the UV sample time, number of the UV data samples and UV data resolution are wirelessly transmitted 530 to the wearable unit 200 to determine if configuration update is necessary 625. Based on the received commands 625, the wearable unit 200 will either keep previous configurations 630 or set new configurations 635 for measuring UV data 640. These configurations determine how the UV data is measured and how often the data is wirelessly transmitted to the mobile computing device 100. For example, if a user wants to know the current UVI irradiating on the wearable unit 200, the data can be immediately sampled and transmitted to the mobile computing device 100. If the mobile computing device 100 is not in close proximity of the user 645, the sampled UV data can be temporarily stored in the local memory 650 of the wearable unit 200 for later transmission whenever the mobile computing device 100 is within the range to establish a pairing connection. In order to save the wearable unit battery consumption, all or parts of the electronic circuitries especially the wireless communication circuit could be powered down into a sleep mode 665, which consumes a minimal power. The wearable unit 200 goes into sleep mode whenever there is no active data sampling/processing or communication with the mobile computing device 100, and typically wakes up automatically 675 according to configured sampling period and communication protocol. A limited data processing and calculation on the wearable unit 200 can be implemented to reduce a firmware complexity on the microprocessor 250 and minimize the wake-up time for power saving. Therefore, most of the post data processing such as calculation of UV dose and vitamin D generation can be performed in the mobile computing device 100 as illustrated in FIG. 2. The results of the calculation can be sent back to the wearable unit 200 through wireless communication. Alternatively, if the mobile computing device 100 is out of the communication range of the wearable unit 200, the data processing and calculation could be performed by the microprocessor 250 on the wearable unit 200. If the calculated data results in a necessary user alert 545, the alarm mechanism is activated. The alarm mechanism could be an alarm sound, flashing screen/light or vibration generated by the mobile computing device 100, or the wearable unit 200, or both. For example, the alarm can be generated by the mobile computing device 100 to display related alarm information 550. Meanwhile, an alarm command 660 can be sent to the wearable unit 200 which also generates a user perceptible light and/or vibration alert 670.

As shown in FIG. 2, communication between the wearable unit 200 and the mobile computing device 100 is periodic for maintaining connection. The polling mechanism where one device broadcasts data and waits for another device acknowledges is used for notifying the connection status. If the time between broadcasting and waiting for acknowledgment is beyond a programmable communication time-out, connection is lost. With several failing reconnection attempts, the sampled UV data is then stored in the local memory circuit 650. Whenever the mobile computing device 100 is within the range 645 to establish a successful connection, the previously stored data is automatically transmitted 655 to the mobile computing device 100. By evaluating the received signal strength sent by the wearable unit 200, the mobile device 100 can implement the electronic leash function to estimate the distance to the wearable unit 200 and determine if it is within or outside the communication range.

Since the wearable unit 200 and the mobile computing device 100 are coupled together via wireless communication, the periodic status updates such as electronic leash notification, battery indication and memory indication can be wirelessly transmitted along with the measured UV data. Alarm can be generated by the wearable unit 200, or the mobile computing device 100, or both to alert the user of abnormal system conditions (e.g. memory full, low battery, communication lost, etc.). Therefore, it allows the UV dosimetry system operate without any interruptions due to electronic unleash, low battery or lack of memory. As a result, the accuracy and reliability of the system increases.

General Description of the User Interface

The wearable unit is by default in a sleep mode and the user can activate the measurement of the UVI, UV dose, and vitamin D production. The mobile device app can start, pause, resume, stop, and reset the measurement. The wearable unit can also start, pause, resume, and reset the measurements with user input, such as finger taps on a touch sensing area. For example, different numbers and/or sequences of taps can mean different commands.

The mobile device and the wearable unit can trigger sound, light, or vibration alarms when the accumulated UV dose is close to the harmful level. The wearable unit can also indicate the status or measurement results such as UVI, for example, with a few LEDs laid out in a circle or line. The mobile device can instantly query the measurements from the wearable unit. It can also display, store, edit, analyze, and provide summary report of the data collected by the wearable unit.

The mobile application syncs with a remote server to save the sensor measurement data in a secure database. This data becomes accessible from other mobile devices or directly from a webpage protected by a password. Using a software application, the data can be analyzed and presented in easy to understand graphs, tables, and summary reports. The user can share the data through social media, email, or text message.

Annotations can be added to the data for tagging purposes. For example, through annotation, the user can then remember when the data has been taken. The user can also annotate relevant events such as applying a sunscreen lotion, changing clothes, staying indoors, taking vitamin D supplement, etc.

The UV dosimetry system can accurately measure the location specific UVI in real time, which is more precise than the UVI forecast predicted by weather services. The UVI measurement by a user wearing the wearable unit can be posted in crowd sourcing websites or on a dedicated server and shared in the mobile device app so that anybody can access it. Since the UVI measurement could be misleading, e.g. if the user is in the shade, the app takes into account the forecasted UVI and/or the temperature of the device to decide if the measurement is valid or not. If it is valid then it is pushed to the servers. Otherwise it is discarded.

The mobile device also provides a user interface that allows user to change profile settings (e.g. age, gender, height, weight, etc.) and/or programming parameters. For example, user can select options and/or parameters that affect the calculation of UV dose and vitamin D production, such as clothing coverage, sunscreen type, etc.

Method for Multi-User Management

Multiple users can take advantage of one single wearable unit. The mobile app can create several accounts protected by a password. Each account saves its own data associated with one individual user. In addition, each account can create several profiles for the associated user. A profile is a configuration for a specific measurement of UV dose and/or vitamin D production. For example, it can include the clothes type worn and the sunscreen SPF used. Profiles are used to avoid setting the same parameters multiple times.

The mobile application can also track several wearable units at the same time. Each wearable unit can trigger a different alarm and an electronic leash allows the app to detect when a wearable unit is out of range by setting a sound, vibration, or light alarm on the mobile device and/or the wearable unit. Multi-user tracking is convenient, for example, for a parent or a caregiver to monitor UV exposure of several children.

In addition, by utilizing the electronic leash function, the mobile device can operate in a search mode that allows the mobile app to find a lost wearable unit.

Method for Calculating the UV Dose

According to this disclosure, the UV dosimetry system is capable of real time measuring and logging of accumulated UV irradiation dose received by a person. The wearable unit includes a UV sensor that accurately measures the UV irradiance intensity (both UVA and UVB) in a continuous manner. The UV dosimetry system automatically integrates the measured UV irradiance intensity over time to obtain a sensor site specific UV dose. The UV dosimetry system can further adjust the sensor site specific UV dose by taking into account factors such as UV sensor location, body surface area, clothing coverage, and sunscreen usage, to derive a total absorbed dose. In addition, the standard UVI is also calculated in real-time, and can be used for crowd sourcing in a network.

According to one embodiment, the UV sensor used in this wearable unit comprises one photodiode with a broadband spectrum enclosed in a waterproof case. An amplifier converts the photo-current to voltage depending on the UV irradiance intensity. The spectral sensitivity characteristics of the photodiode closely match the erythemal action spectrum, and are highly sensitive and specific to the UVA and UVB. In an alternative embodiment, the UV sensor comprises a plurality of photodiodes each of which has a unique UV spectral response, whereas all together these photodiodes cover the broadband UV spectrum, and the overall spectral sensitivity characteristics of these photodiodes closely matches the erythemal action spectrum. Standard calibration procedure is performed in advance so that the output of the UV sensor is a voltage signal that is proportional to the intensity of UV irradiances within the UVA and UVB spectrum. The measured UV intensity can be expressed in as power per unit area, e.g. watt (W) per square meter (W/m$^2$). This UV sensor output voltage signal is further filtered, then sampled through an analog-to-digital converter (ADC), and then fed to the input of a microcontroller for further digital signal processing. Alternatively, the sensor measured data can be wirelessly sent to the mobile computer device for further signal processing. It should be understood that all calculations including the data processing steps described below can be performed in the wearable unit alone, or in the mobile computing device alone, or by both the wearable unit and the mobile computing device of the UV dosimetry system (e.g. through distributed computing whereby some of the simple calculations are done by the wearable unit while other more complex calculations are done by the mobile computing device).

It is known that the UV intensity is related to the UV index according to the formula UV intensity (W/m$^2$)=UVI×0.025 (W/m$^2$)

Therefore, the UVI can be calculated in real time based on the measured UV intensity.

In one embodiment, the UV dosimetry system automatically calculates the sensor site specific UV dose in real-time, by integrating the UV irradiance intensity over time. The duration of the integration is typically from the last device reset time to the instantaneous time of the UV irradiance intensity measurement. The device reset can be manually performed by the user, or automatically performed at specific time of the day, e.g. at the midnight. The numerical integration can be implemented based on the Newton-Cotes formulas, such as the trapezoid rule of integration. Specifically, the UV dose can be calculated as:

$$D(t) = \left[\sum_{k=0}^{t}(I_k + I_{k+1}) \cdot (t_{k+1} - t_k)\right] / 2,$$

where D(t) is the accumulated UV dose until time t (assume time starts with 0), $I_{k+1}$ and $I_k$ are respective UV intensity readings at two consecutive sample times $t_{k+1}$ and $t_k$.

The result of the time integration of the UV intensity signal calculated above is the sensor site specific dose, since it measures the total amount of the UV irradiances over a specified duration that is received by the UV sensor at the specific measuring site. Based on pre-calibration of the UV sensor which has predetermined active optical aperture area, the sensor site specific dose ($D_{sensor}$) is expressed as UV irradiance energy per unit area, e.g. joules per square meter (J/m$^2$). When the sensor site specific UV dose exceeds a user programmable safety limit, skin damage (e.g. sun burn) can occur to the exposed skin near the sensor site. Thus, alarm can be generated by the UV dosimetry system when the measured $D_{sensor}$ approaches the safety limit, which can be user programmable.

Because $D_{sensor}$ only represents the amount of UV irradiance dose received by the UV sensor, it needs to be adjusted based on the effective body surface area (BSA) to reflect the total UV irradiance dose received by the subject. This adjustment takes multiple steps. In the first step, it is assumed that the whole BSA is exposed to UV irradiance that has the same radiation intensity as the UV sensor site. Then the full body surface area UV irradiance dose ($D_{full-BSA}$) can be calculated by multiplying the sensor site specific dose by the BSA: $D_{full-BSA}=D_{sensor} \times BSA$. The full body UV irradiance dose has the energy unit, e.g. Joules. There are several different models that can be used to calculate the BSA based on the subject's height and weight. One representative model is the DuBois and DuBois formula which has been shown to have good accuracy over a wide range of different populations with various types of body shape: BSA (m$^2$)=0.20247×Height (m)$^{0.725}$×Weight (kg)$^{0.425}$. Both height and weight information can be previously entered into the UV dosimetry system by the user.

Because the UV radiation intensity is not uniform over the body surface, the calculated full body surface area UV irradiance dose ($D_{full-BSA}$) can be adjusted based on the sensor location. A sensor location factor (SLF) can be predetermined based on the wearing site of the sensor on the body, the local latitude, and the season of year. The latitude and season can affect the SLF because the solar angle changes throughout the year and varies geographically. The wearing site can also affect SLF because some areas of the body (e.g. neck and face) generally receive more sunlight than other areas (e.g. waist). The SLF can be calculated by means of geometric modeling, similar to the method that is described in the paper by Pope and Godar, "Solar UV geometric conversion factors—Horizontal plane to cylinder model" Photochemistry and Photobiology, 2010; 86:457-466. Alternatively, the SLF can be pre-calibrated by means of an experimental study involving a group of subjects wearing multiple UV sensors at different parts of the body, as exemplified by the approach described by Thieden et al. "The wrist is a reliable body site for personal dosimetry of ultraviolet radiation." Photodermatol Photoimmunol Photomed 2000; 16: 57-61. Thus, the sensor location adjusted full body surface area UV irradiance dose ($D_{adj-full-BSA}$) can be calculated as $D_{adj-full-BSA}=D_{full-BSA} \times SLF$.

Because of clothing coverage, the sensor location adjusted full body UV irradiance dose need to be further adjusted to reflect the actual UV radiation over the exposed body surface area. For this adjustment, the user can select through the software app to define the actual clothing coverage. The device also stores a series of Lund-Browder charts. The Lund-Browder charts have been widely used in burn medicine to assess the burned BSA. These charts quantitatively characterize the surface area of each major section of the body (head, neck, anterior and posterior torso, arms, legs, etc) as a percentage of the total BSA, taking into account of age since children have smaller extremities but larger heads than adults. Linearly interpolated values can be found between ages on the Lund-Browder charts. In addition, modified Lund-Browder chart values can be used for obese adults. In one exemplary embodiment, the software app provides an avatar as a graphical representation of the user. The user can select different clothing combinations for different parts of the body by browsing through or toggling between various clothing options. For example, the user can select no hat, baseball cap, or cowboy hat to represent different degrees of head coverage. Likewise, the user can select bare chest, short sleeve, or long sleeve to represent different degrees of upper body coverage. Clothing coverage for other parts of the body surface can be similarly defined. The selection of clothing options can vary in number and styles. Each selected clothing option has a predefined surface area coverage percentage for the selected body part. In addition, customized clothing option is available for user to edit the percentage of body area coverage for the user-defined clothing. Based on user selected clothing coverage and the device stored Lund-Browder charts, the ratio between exposed BSA and the total BSA, $f_{BSF}$, can be calculated. The ratio $f_{BSF}$ ranges from 0 to 1, where 0 corresponds to complete body coverage (no skin exposure) and 1 corresponds to complete BSA exposure (no clothing coverage). Then adjustment can be made to derive the exposed body surface area UV irradiance dose: $D_{exposed-BSA}=D_{adj-full-BSA} \times f_{BSF}$.

To derive total absorbed dose by the subject, the exposed body surface area UV irradiance dose should be further adjusted based on skin color, sunscreen usage, and clothing fabric. Different skin color can have different UV light sensitivity. The built-in camera of the mobile computing device (e.g. the built-in camera of the smart phone) may be used as a colorimeter, to take the skin image and automatically determine the skin color. Weighting factors corresponding to different skin colors ($f_{color}$) can be predetermined, and are used to adjust the exposed body surface area UV irradiance dose. Application of sunscreen product can also block the body's absorption of UV irradiance. Sunscreen's UV protection efficacy depends on its ingredients and is typically represented by its labelled sun protection factor (SPF). For example, the Environmental Working Group (EWG) has published a quantitative method to evaluate the efficacy of sunscreen, by taking into account multiple factors such as the UVA and UVB absorbance spectra for active ingredients, the balance of UVA/UVB protection, the stability of active ingredient combinations, etc. Therefore, weighting factors corresponding to different sunscreen products ($f_{sunscreen}$) can be predetermined based on the active ingredients used in the product or the product's SPF value, and are used to adjust the exposed body surface area UV irradiance dose. For example, if a user applies a layer of sunscreen with effective SPF value of 50 during a period of time, then the effective UV irradiance dose received by the user is reduced to 2% of the UV dose corresponding to no sunscreen usage, i.e. the $f_{sunscreen}$ can be approximately set to 1/50 in this example.

In addition, the UV protection factor (UPF) of clothing varies depending on the fabric types and fabric colors. The skin surface covered beneath clothing with low UPF may still receive certain amount of UV radiation. The UV irradiance dose received by the clothing covered body surface area can be estimated as: $D_{covered-BSA}=D_{adj-full-BSA} \times (1-f_{BSF}) \times f_{clothing}$, where $f_{clothing}$ is a predetermined weighting factor that takes into account the UPF of the wearing clothing. In most cases where the UV irradiance penetrating the clothing is negligible, $f_{clothing}$ can be approximately set to 0.

Therefore, the total UV dose received by the subject can be calculated as the sum of exposed body surface area UV irradiance dose ($D_{exposed-BSA}$) adjusted for skin color and sunscreen usage, and the clothing covered body surface area UV irradiance dose ($D_{covered-BSA}$), adjusted for skin color (assuming no sunscreen use under the clothing). That is, $D_{total}=D_{exposed-BSA} \times f_{color} \times f_{sunscreen} D_{covered-BSA} \times f_{color}$.

Method for Calculating the Vitamin D Production

According to this disclosure, the UV dosimetry system measures the UV irradiance in real-time and calculates the daily vitamin D production. Because the spectral sensitivity characteristics of the UV sensor embedded in the wearable unit closely matches the erythemal action spectrum, the daily UV irradiance dose measured by the wearable unit can be expressed in terms of standard erythemal dose (SED, 1 SED=100 J/m$^2$), which is independent of the spectral output of the source and the individual's skin type. The daily SED is calculated by the wearable unit by integrating the UV sensor measured UV irradiance intensity over a day. The calculated daily SED is then used to estimate the daily vitamin D production according to the following formula: Vitamin D (IU)/day=SED/day×ASCF×GCF×4900 IU×STF×FBE×AF. Here, ASCF is the action spectrum conversion factor that is used to change erythemally weighted to previtamin D3-weighted UV doses. The geometric conversion factor (GCF) is used to convert horizontal plane UV irradiances to average irradiances on the human body. The wearable sensor location factor (SLF) described above can also be incorporated for adjustment of the GCF. The STF is the skin type factor, wherein the skin type is classified according to the Fitzpatrick scale, which can be predefined by the user or automatically determined by using the built-in camera of the mobile computing device as a colorimeter. The FBE is the percent body exposure that can be estimated from the Lund-Browder charts as described above. The AF refers to the age factor since the capability of vitamin D production decreases with age. These factors are described in Godar et al.: Solar UV doses of young Americans and Vitamin D3 production. Environmental Health Perspectives, 2012; 139-143. In addition, the application of sunscreen product also affects vitamin D production. The weighting factor $f_{sunscreen}$ described above can be used to adjust the calculated vitamin D production. For example, if a user applies a layer of sunscreen with effective SPF value of 50 throughout the day, then the effective daily vitamin D produced by the user is reduced to 2% of the vitamin D production corresponding to no sunscreen usage, i.e. the $f_{sunscreen}$ can be approximately set to 1/50 in this example. By providing quantitative measurement of daily vitamin D production, one can objectively assess whether the amount of sun exposure is too much or too little. On one hand, one can avoid over exposure of sunlight to avoid the detrimental health effect. On the other hand, one with vitamin D deficiency can be more motivated to be exposed to sunlight or be more informed on how much vitamin D supplement should be taken. Thus the disclosed UV dosimetry system can provide a useful tool to guide people to optimally balance between the detrimental effects and health benefits of UV exposure.

Method for Crowd Sourcing of UVI Data

According to this disclosure, UVI at various geographical locations is measured and updated in real-time by a large number of UV measurement devices, or UV meters, by means of crowd sourcing method. People who are using UV meters such as the disclosed UV dosimetry system, are encouraged to provide the real-time UVI data together with the time (e.g. using the build-in clock of the mobile device) and location information (e.g. via GPS embedded in the mobile computing device) through the wireless network to a remote server, for example, in exchange for a credit or discount coupon to be used toward certain products or services. Users who opt to provide data can be anonymous to protect their identities.

The remote server maintains a database containing the data transmitted from the UV meters. A user "pushes" the measured data (UVI, time, location) to the remote server in triggered mode, automatic mode, or mixed mode. In triggered mode, the user initiates the data transmission by sending a command through the user input interface of the mobile computing unit to instruct the mobile application start the communication session. In automatic mode, the mobile application is configured to exchange data with the remote server on periodic basis, e.g. at programmed time of the day or at programmed time intervals. In mixed mode, both manual triggered and automatic data transmission are supported. Frequency of the data transmission can be limited (e.g. not more than 1 time per×minutes, where X is a programmable parameter that defines the shortest duration between two consecutive data transmissions) to prevent repeated transmission of the same UVI data.

In one embodiment, the UV dosimetry system also has a build-in temperature sensing unit such as a temperature sensor, and the measured temperature data is also sent to the remote server, together with the measured UVI data and the time and location information of the measurement.

The remote server runs a database management software operative to analyze the data transmitted from the UV meters including UVI, time, location, and/or temperature measurement, and generates UVI maps for other users to use. The UVI maps are preferably updated periodically according to a predefined time interval.

According to this disclosure, the remote server maintains a database that aggregates the data transmitted from the UV measurement devices. The database management software controls the quality of the data collection through a plurality of filters with programmable parameter settings. Quality control of crowd sourced data is important because invalid UVI measurements may be inadvertently sent by the users. For example, a person staying indoors or under the shade may not measure the actual UVI in the local area accurately. Such misleading UVI data shall be excluded from the database.

In one exemplary embodiment, the database management software in the remote server retrieves forecasted UVI data and/or temperature data at different time and geographical locations from trusted sources or official websites, e.g., www.epa.gov, www.weather.gov, etc. User transmitted UVI measurement and/or temperature measurement data are compared with the forecast data at the corresponding time and location. Here, the corresponding time means that the difference between the time of the forecast data and the time of the UVI and/or temperature measurement is below a predefined time limit, e.g. 10 minutes, and the corresponding location means the distance between the location of the forecast data and the location of the UVI and/or temperature measurement is shorter than a predefined distance limit, e.g. 1 mile. User transmitted measurement data is deemed invalid if there is substantial deviation between measured data and the corresponding forecast data, e.g. if they differ by more than a predefined tolerance value.

In another exemplary embodiment, the official forecast data is only used as a reference to reject invalid measurement data when the sample size of the measurement data at specific time period and location is limited. As more user transmitted measurement data at specific time period and location is available and included in the database, the weight of using official forecast data as a reference is reduced. Meanwhile, more weight is given to the user transmitted data, which can self-serve as the reference to reject invalid user input.

For example, when the sample size of UVI and/or temperature data measured during a specific time period and from a specific location is sufficiently large (e.g. greater than a predefined threshold), the expected normal range of UVI and/or temperature at said specific time period and location can be calculated based on the statistical distribution of the measured UVI and/or temperature data (e.g. the mean and standard deviation, or the median and inter-quartile range). Outlier measurement data falling outside the expected normal range will then be deemed invalid.

For the UVI (or temperature) data at specific time and specific location, the sample size is defined as the total number of UVI (or temperature) data measured during a time period that is close to said specific time (e.g. within a predefined time interval), and from a region that is centered around said location (e.g. within a predefined distance).

Through crowd sourcing, the UVI data is updated in the remote server database in real-time, and the UVI map can be updated periodically according to a predefined frequency. As more users contribute to the database, the reliability and accuracy of the data increases. The coverage of the UVI data on the map can be as broad as the users can go and the spatial resolution can be as fine as the GPS allows. It also allows people who do not have a UV measurement device to obtain real-time UVI information by accessing the crowd sourced UVI database through a communication network, such as the internet.

While the invention has been described with reference to exemplary embodiments, it shall be understood by those skilled in the art that various changes may be made and equivalents may be substituted without departing from the scope of the invention. In addition, many modifications may be made to adapt a particular situation or component to the teachings of the invention without departing from its scope. Therefore, it is intended that the invention not be limited to the particular embodiment disclosed, but that the invention will include all embodiments falling within the scope of the appended claims.

We claim:

1. A system for crowd sourcing of UV measurement data with improved quality control, the system comprising:
   a remote server; and
   a plurality of UV meters, each of the plurality of UV meters comprises:
      a circuitry for measuring irradiating UV intensity and corresponding UV index (UVI);

a location tracking unit for measuring a location of said UV meter;

a clock unit for measuring time; and a communication unit operative to transmit data to said remote server through a communication network, and duration between two consecutive data transmissions is configured to be greater than a programmable value so as to prevent repeated transmission of same data;

said remote server running a database management software operative to generate UVI maps wherein the database management software comprises a filter that is adapted to remove invalid UVI measurement data received at a specific time from a specific location, wherein the invalid UVI measurement data comprises UVI data that falls outside an expected normal range of UVI calculated based on a statistical distribution of all UVI data measured during a time period centered around said specific time with a predefined time interval and from a region centered around said specific location with a predefined distance.

2. The system of claim 1, wherein said UVI maps show a distribution of UVI data at different locations measured by the plurality of UV meters at different times, excluding the invalid UVI measurement data; and said UVI maps are updated periodically according to a predefined time interval.

3. The system of claim 2, wherein said remote server provides a user interface supporting remote user access of said UVI maps through a communication network.

4. The system of claim 2, wherein each of the plurality of UV meters is configured to transmit data to said remote server automatically on periodic basis, or manually triggered by a user's command through a user input interface of said UV meter, and the frequency of data transmission is limited by a programmable value defining the shortest duration between two consecutive data transmissions.

5. The system of claim 1, wherein said remote server is configured to receive forecast UVI at different time and locations from predefined sources.

6. The system of claim 5, wherein the detected invalid UVI measurement data comprises UVI data that deviates from the forecast UVI at said specific time and location by more than a predefined tolerance value.

7. The system of claim 6, wherein the filter is adapted to remove the invalid UVI measurement data based on the forecast UVI when a sample size of the measured UVI data is smaller than or equal to a predefined threshold, and based on the measured UVI data when its sample size exceeds said predefined threshold.

8. The system of claim 1, wherein each of the plurality of UV meters further comprises a temperature sensing unit for measuring a local temperature, and is operative to transmit the measured local temperature data together with the concurrently measured UVI data to said remote server.

9. The system of claim 8, wherein the invalid UVI measurement data comprises UVI data that has the concurrently measured local temperature falling outside an expected normal range of temperature calculated based on a statistical distribution of all temperature data measured during a time period centered around said specific time with a predefined time interval and from a region centered around said specific location with a predefined distance.

10. The system of claim 8, wherein said remote server is configured to receive forecast temperature at different time and locations from predefined sources; and the invalid UVI measurement data comprises UVI data that has the concurrently measured local temperature deviating from the forecast temperature at said specific time and location by more than a predefined tolerance value.

11. A method for crowd sourcing UV measurement data with improved quality control, the method comprising:

measuring UVI by a plurality of UV meters, and tracking location and time of UVI measurement by said plurality of UV meters;

transmitting measured UVI, location, and time data measured by said plurality of UV meters to a remote server through a communication network, and duration between two consecutive data transmissions is configured to be greater than a programmable value so as to prevent repeated transmission of same data;

processing said measured UVI, location, and time data by a database management software running on said remote server to generate UVI maps, wherein the database management software comprises a filter that is adapted to remove invalid UVI measurement data received at a specific time from a specific location, wherein the invalid UVI measurement data comprises UVI data that falls outside an expected normal range of UVI calculated based on a statistical distribution of all UVI data measured during a time period centered around said specific time with a predefined time interval and from a region centered around said specific location with a predefined distance.

12. The method of claim 11, wherein said UVI maps show a distribution of UVI data at different locations measured by the plurality of UV meters at different times, excluding the invalid UVI measurement data; and said UVI maps are updated periodically according to a predefined time interval.

13. The method of claim 12, wherein each of the plurality of UV meters is configured to transmit data to said remote server automatically on periodic basis, or manually triggered by a user's command through a user input interface of said UV meter.

14. The method of claim 11, wherein said remote server provides a user interface supporting remote user access of said UVI maps through a communication network.

15. The method of claim 11, wherein said remote server is configured to receive forecast UVI at different time and locations from predefined sources.

16. The method of claim 15, wherein the detected invalid UVI measurement data comprises UVI data that deviates from the forecast UVI at said specific time and location by more than a predefined tolerance value.

17. The method of claim 16, wherein the filter is adapted to remove the invalid UVI measurement data based on the forecast UVI when a sample size of the measured UVI data is smaller than or equal to a predefined threshold, and based on the measured UVI data when its sample size exceeds said predefined threshold.

18. The method of claim 11, wherein each of the plurality of UV meters further comprises a temperature sensing unit for measuring a local temperature, and is operative to transmit the measured local temperature together with concurrently measured UVI data to said remote server.

19. The method of claim 18, wherein the invalid UVI measurement data comprises UVI data that has the concurrently measured local temperature falling outside an expected normal range of temperature calculated based on a statistical distribution of all temperature data measured during a time period centered around said specific time with a predefined time interval and from a region centered around said specific location with a predefined distance.

20. The method of claim 18, wherein said remote server is configured to receive forecast temperature at different time and locations from predefined sources; and the invalid UVI measurement data comprises UVI data that has the concurrently measured local temperature deviating from the forecast temperature at said specific time and location by more than a predefined tolerance value.

* * * * *